United States Patent [19]  [11] 3,985,812
Del Bel et al. [45] Oct. 12, 1976

[54] CAUSTIC REFINING OF 2,3,6-TRIMETHYLPHENOL

[75] Inventors: Elsio Del Bel, Bethel Park; Donald C. Jones; Martin B. Neuworth, both of Pittsburgh, all of Pa.

[73] Assignee: Continental Oil Company, Ponca City, Okla.

[22] Filed: Nov. 14, 1974

[21] Appl. No.: 523,626

Related U.S. Application Data

[63] Continuation of Ser. No. 764,429, Oct. 2, 1968, abandoned.

[52] U.S. Cl. .......................... 260/621 B; 260/621 A
[51] Int. Cl.² ................... C07C 37/38; C07C 37/44
[58] Field of Search ..................... 260/621 A, 621 B

[56] References Cited

UNITED STATES PATENTS

| | | | |
|---|---|---|---|
| 2,260,683 | 10/1941 | Robbins et al. | 260/621 B |
| 2,581,406 | 6/1952 | Golumbic et al. | 260/621 B |
| 3,517,072 | 6/1970 | Moroni et al. | 260/621 B |

*Primary Examiner*—Norman Morgenstern
*Attorney, Agent, or Firm*—Cortlan R. Schupbach, Jr.

[57] ABSTRACT

2,3,6-Trimethylphenol is recovered in high yield and high purity from its admixture with di- and tri- methyl-substituted phenols by subjecting the admixture in a solvent to countercurrent caustic extraction.

3 Claims, 1 Drawing Figure

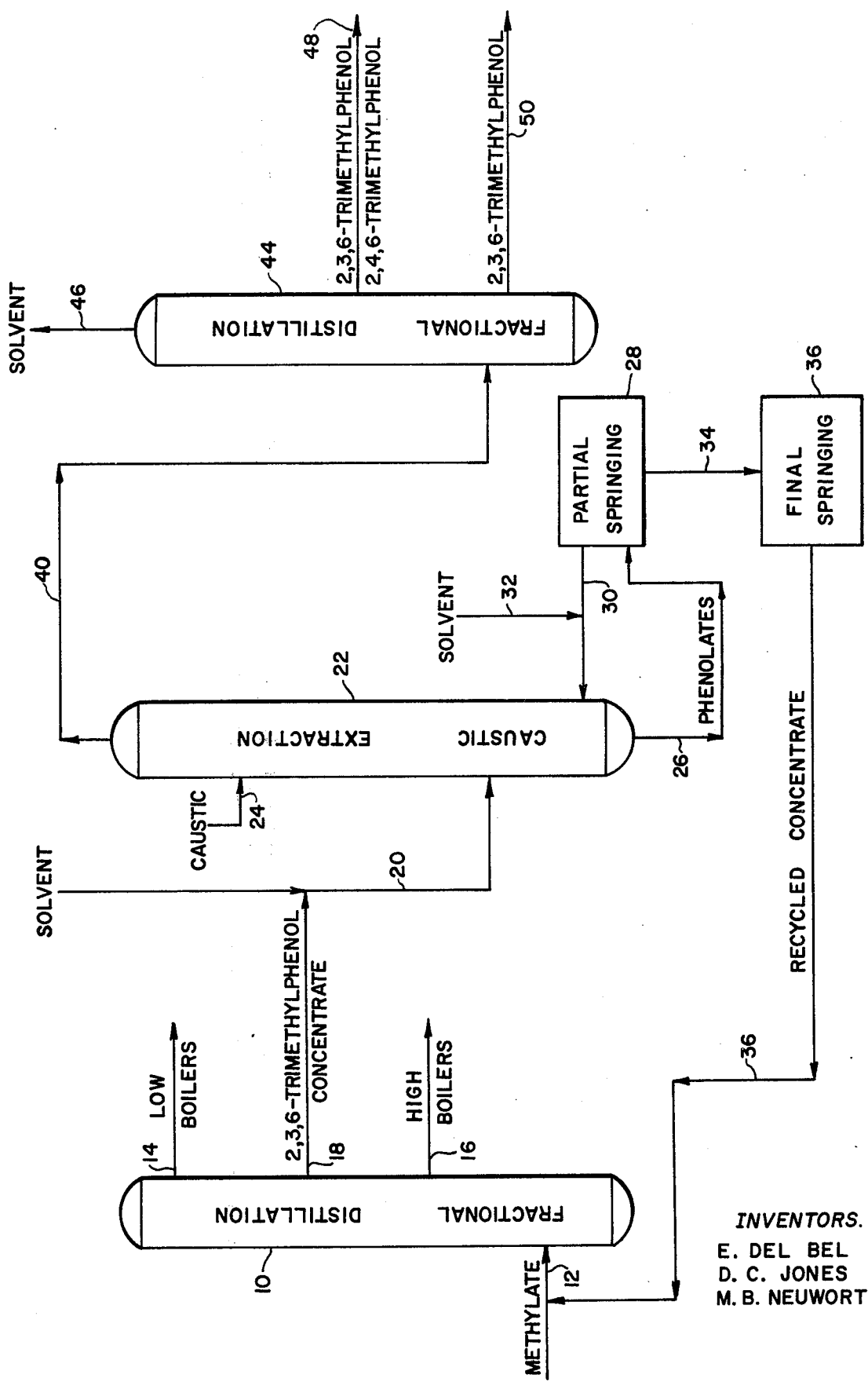

CAUSTIC REFINING OF 2,3,6-TRIMETHYLPHENOL

This is a continuation of application Ser. No. 764,429 filed Oct. 2, 1968 now abandoned.

This invention relates to a process for separating 2,3,6-trimethylphenol from its admixture with closely boiling di- and tri-methyl-substituted phenols.

2,3,6-Trimethylphenol is useful as an intermediate in the commercial preparation of vitamin E. The compound is first converted to the corresponding trimethylhydroquinone (see Journal of Organic Chemistry, Vol 4:318 et seq. (1939)). The latter is then converted to vitamin E (see Encyclopedia of Chemical Technology, Vol 14:852).

Methylation of phenol by methanol in the vapor phase over activated alumina at a temperature between 300° and 350° C. produces a mixture of cresols, xylenols, trimethylphenols and higher boiling homologs. Major components of the isomeric trimethylphenols are 2,3,6-trimethylphenol and 2,4,6-trimethylphenol. The 2,3,6-trimethylphenol can be concentrated to about 50 percent by fractionation of the methylate product. A second fractionation results in the recovery of relatively pure (95–96%) 2,3,6-trimethylphenol, but the yield is low (less than 50%). For example, when a mixture containing 55.7 percent (wt.%) 2,3,6-trimethylphenol, 13.8 percent 2,4,6-trimethylphenol, 11.5 percent 2,3-xylenol, 8.2 percent 2,3,5- and 2,4,5-trimethylphenols, 4.1 percent 2,4- and 2,5-xylenols and lesser amounts of cresols, other xylenols and tri- and tetramethylphenols was fractionated in a 25 theoretical plate column at 400 mm. Hg and at reflux ratios of 25/1, the recovery of 2,3,6-trimethylphenol of 95.3 percent purity was only 48 percent. As can be seen from the boiling points listed in Table I below, the principal components which make this fractionation difficult are 2,3-xylenol, 3,4-xylenol, 3,5-xylenol and 2,4,6-trimethylphenol.

TABLE I

| | Boiling Points, °C. | | |
|---|---|---|---|
| | 100 mm.Hg | 400 mm.Hg | 760 mm.Hg |
| 2,4-Xylenol | 143 | 186 | 210 |
| 2,5-Xylenol | 143 | 186 | 210 |
| 2,3-Xylenol | 150 | 193 | 218 |
| 2,4,6-Trimethylphenol | 153 | 198 | 219.5 |
| 3,5-Xylenol | 155 | 197 | 222 |
| 2,3,6-Trimethylphenol | 158 | 202 | 225 |
| 3,4-Xylenol | 160 | 203 | 226.7 |
| 2,3,5-Trimetylphenol | 165 | 208 | 232 |
| 2,4,5-Trimethylphenol | 165 | 208 | 233 |
| 2,3,4-Trimethylphenol | — | — | 235.7 |

In accordance with our invention, a process is provided for recovering 2,3,6-trimethylphenol from its admixture with 2,4,6-trimethylphenol and other closely boiling di- and tri-methyl-substituted phenols in better than 95 percent purity and with 75 percent yield. The process comprises, in its broadest aspects, countercurrent caustic extraction to yield a raffinate containing principally 2,3,6-trimethylphenol and 2,4,6-trimethylphenol followed by fractional distillation of the caustic unsoluble raffinate to recover 2,3,6-trimethylphenol in high purity. We have discovered that caustic extraction will produce a raffinate which is readily fractionated to yield a fraction containing 2,3,6-trimethylphenol of the aforesaid purity and in the aforementioned yield. Caustic extraction almost completely removes 2,3-xylenol, 3,4-xylenol and 3,5-xylenol in the extract, leaving 90 percent or more of the 2,3,6- and 2,4,6-trimethylphenols in the raffinate. Any phenol, cresols and other xylenols which are present are also removed along with part of the other trimethylphenols (i.e. 2,3,4-, 2,3,5-, 2,4,5-, and 3,4,5-trimethylphenols). When the resulting raffinate is fractionated at 400 mm. Hg in a 25 theoretical plate column, the recovery of 2,3,6-trimethylphenol of 95.4 percent purity is 74.5 percent.

More specifically, in accordance with our invention, a phenol methylate fraction is first obtained which contains at least 40 percent by weight of 2,3,6-trimethylphenol. This mixture, dissolved in a solvent, is subjected to countercurrent extraction with aqueous alkali metal hydroxide in which the concentration of the alkali metal hydroxide is between 2 and 10 percent by weight, and preferably between 4 and 6 percent. The ratio of moles of alkali metal hydroxide to moles of extractables is between 0.9 and 2.0, and preferably between 1.2 and 1.6. The term "extractables" as used herein means any phenol, cresols, xylenols and 25 percent by weight of the trimethylphenols other than 2,3,6-trimethylphenol and 2,4,6-trimethylphenol present in the feedstock. The raffinate, i.e. the solvent stream, is fractionated to recover the 2,3,6-trimethylphenol.

For a better understanding of our invention, its objects and advantages, reference should be had to the following description of the preferred embodiment and to the accompanying drawing in which the preferred embodiment is schematically illustrated.

Referring to the drawing, numeral 10 designates a commercial fractional distillation column having, for example, the equivalent of 50 plates. To this column is fed through a conduit 12 a liquid stream of phenol methylate (i.e. the product of catalytic methylation of phenol with methanol at a temperature between 300° and 350° C.) containing unreacted phenol, cresols, xylenols, trimethylphenols, and higher methyl-substituted phenols. The fractional distillation column is operated to obtain a fraction having a 2,3,6-trimethylphenol concentration of at least 40 percent by weight and preferably above 50 percent. If a single column does not achieve the desired concentration, then it is necessary to employ a series of columns in which the 2,3,6-trimethylphenol is progressively concentrated in the desired fraction. Lower boiling and higher boiling fractions of the distillate feed are withdrawn through conduits 14 and 16 respectively.

The 2,3,6-trimethylphenol concentrate is withdrawn from the fractional distillation column 10 through a conduit 18 and dissolved in a solvent admitted through a conduit 20. The solvent is preferably a hydrocarbon which boils between 60° and 150° C., for example, toluene. Other solvents which may conveniently be used are benzene, hexane and heptane. The ratio of solvent to concentrate is such as to minimize the final volume of solution. Generally the concentration of phenols in the solution is between 60 and 75 percent by weight. The solution is introduced into the lower portion of a vertical countercurrent extraction column 22. At the same time, a solution of aqueous alkali metal hydroxide, preferably sodium hydroxide or potassium hydroxide, is introduced through a conduit 24 into the upper portion of the column. The concentration of the hydroxide is less than 10 percent by weight, and preferably between 4 and 6 percent by weight. The selected solvent is one which has a specific gravity that assures a solution of the 2,3,6-trimethylphenol concentrate lighter than the aqueous caustic solution. The caustic solution being heavier, flows downwardly in countercurrent flow relationship to the upwardly moving concentrate solution. The rates of flow of the two oppositely flowing streams are regulated so that the mole ratio of alkali metal hydroxide to the extractables is between 0.9 and 2, preferably between 1.2 and 1.6. As the downwardly flowing caustic solution contacts the upwardly moving phenols, the latter, including the 2,3,6-trimethylphenol in part at least, are converted to their alkali metal salts. However, the salts of 2,3,6-trimethylphenol and 2,4,6-trimethylphenol apparently are quickly reconverted to the trimethylphenol form upon contacting unconverted xylenols entering from conduit 20. This conclusion is confirmed by the complete absence of any xylenols in the hydrocarbon solution leaving the top of the column. Since the aggregate concentration of the trimethylphenols in the solvent steadily increases as the solvent advances up the column, it is desirable to maintain the temperature in the column sufficiently high to prevent crystallization of trimethylphenols. A suitable temperature is 50° C. Of course, excess solvent can be used to prevent such crystallization, but additional solvent reduces the throughput and is, therefore, undesirable.

The downwardly moving stream of caustic solution which consists essentially of the phenolates is withdrawn from the bottom of the column through a conduit 26 to a vessel 28. The latter may be simply a tank in which the aqueous phenolate solution is partially sprung, that is, partially converted to phenols by the addition of $CO_2$ or other acid. Two phases are thereby formed in the vessel, the lighter phase consisting of the phenols and the heavier phase of the unconverted phenolates. The phenol phase is recycled to the lower portion of the column 22 through a conduit 30 after being redissolved in solvent added through conduit 32. Such recycle simulates reflux and improves the recovery of 2,3,6-trimethylphenol.

The heavier phase consisting essentially of unsprung phenolates is conducted from vessel 28 through a conduit 34 to a second vessel 36 wherein the phenolates are completely converted to phenols by $CO_2$ or other suitable acid. The sprung phenols, if sufficient 2,3,6-trimethylphenol is present, may be recycled through a conduit 38 to the feed input conduit 12.

The hydrocarbon solution in the extraction column 22 is withdrawn through a conduit 40 to a fractionating column 44. The solvent is removed and separately recovered for reuse if desired. A lower boiling fraction is recovered through conduit 48 which consists essentially of 2,3,6-trimethylphenol and 2,4,6-trimethylphenol, generally in almost equal amounts. This fraction may be readily separated by the butylation-debutylation separation process described and claimed in the application for Letters Patent of D. C. Jones and M. B. Neuworth, filed on even date herewith. A high boiling fraction is recovered through conduit 50 from column 44 which contains 2,3,6-trimethylphenol in better than 95 percent purity, the principal residual contaminant being 2,4,6-trimethylphenol. The yield of 2,3,6-trimethylphenol based upon the feed to caustic extraction is generally about 75 percent.

EXAMPLE

This example describes the separation and recovery of 2,3,6-trimethylphenol from a crude 2,3,6-trimethylphenol concentrate having the composition reported below in Table II.

The extraction apparatus and procedure were as follows. Aqueous sodium hydroxide solution and toluene solution of the crude 2,3,6-trimethylphenol concentrate were charged to lineout and material balance weigh tanks of approximately 9 liters capacity. A 1-inch diameter 28-stage glass Scheibel column was filled with aqueous caustic solution, heated to about 50° C. and stirred at 600 rpm. The aqueous sodium hydroxide solution, metered by rotameter and preheated to 50° C., was introduced above the extraction zone, while the toluene solution of crude 2,3,6-trimethylphenol concentrate, also metered by rotameter and preheated to 50° C., was fed below the extraction zone. Extract was withdrawn from the bottom of the column at a controlled rate to maintain the interface at a constant level which was located just above the caustic feed point. Raffinate overflows from a point just above the interface into a receiver. After an appropriate lineout period (about 1.5 to 2.0 hours), feeds were switched from lineout to material balance weigh tanks, and five consecutive material balance periods were taken. The extract and raffinate from each material balance period were worked up separately and analyzed so that establishment of steady-state conditions was clearly observed. The extracts were neutralized with dilute sulfuric acid and the organic and aqueous layers which formed were separated. The aqueous layer was washed twice with methyl isobutyl ketone (MIBK) and discarded. The MIBK washes were combined with the organic layer and the mixture washed with water and dried. The raffinates were washed twice with water and dried. All contacts between organics and water were made at 50°–60° C. to minimize emulsion problems. Dried extracts and raffinates were analyzed by vapor phase chromotography (VPC).

The conditions and results of an extraction run are shown in Table II below. The data indicate that essentially all the xylenols, as well as any phenol and cresols, are contained in the extract, while 90 percent of the 2,3,6- and 2,4,6-trimethylphenols remain in the raffinate along with the major part of the other trimethylphenols and essentially all the tetramethylphenols.

TABLE II

| Extraction Run No. | | | 1251–22 |
|---|---|---|---|
| Organic feedrate, g/min.[1] | | | 12.55 |
| 5% NaOH feedrate, g/min. | | | 13.80 |
| Moles NaOH per mole extractables | | | 1.28 |
| Total organic material balance, % | | | 101 |
| 2,3,6-Trimethylphenol balance, % | | | 100.3 |
| Recovery of 2,3,6-trimethylphenol in raffinate, % | | | 90.2 |
| | Feed | Raffinate | Extract |
| Weight, grams[2] | 2448 | 1818 | 659 |
| Composition, VPC analyses, wt.% | | | |
| Phenol | tr. | — | tr. |
| o,m,p-Cresols | 0.2 | — | 0.7 |
| Unidentified | 0.3 | 0.3 | — |
| 2,6-Xylenol | 0.3 | tr. | 0.7 |
| 2,4-, 2,5-Xylenols | 4.1 | — | 14.3 |
| 2,3-, 3,5-Xylenols | 11.5 | — | 41.2 |
| 3,4-Xylenols | 1.9 | — | 8.1 |
| 2,4,6-Trimethylphenol | 13.8 | 17.8 | 4.6 |
| 2,3,6-Trimethylphenol | 55.7 | 68.5 | 21.9 |
| 2,3,5-, 2,4,5-Trimethylphenols | 8.2 | 8.5 | 7.3 |
| 2,3,4-, 3,4,5-Trimethylphenols | 2.3 | 2.6 | 1.2 |
| 2,3,4,6-, 2,3,5,6-Tetramethylphenols | 1.7 | 2.3 | tr. |

[1]Contains 35 weight percent toluene.
[2]Solvent-free basis.

The feed to extraction and its raffinate were subjected to comparable fractionations in a 25 theoretical plate, Cannon-packed column at 400 mm. Hg. A narrow boiling fraction (Fraction A) was recovered from the raffinate which was essentially 2,3,6-trimethylphenol. A lower boiling forecut (Fraction B) was also recovered from the raffinate which contained essentially all the 2,4,6-trimethylphenol. Corresponding fractions were obtained from the feed. Table III below tabulates the composition of each of these four fractions.

TABLE III

| Composition, Wt. % | Feed | Raffinate |
|---|---|---|
| | Fraction A | Fraction A |
| Miscellaneous | 0.1 | 0.1 |
| 3,4-Xylenol | 3.3 | — |
| 2,4,6-Trimethylphenol | 0.5 | 3.6 |
| 2,3,6-Trimethylphenol | 95.3 | 95.4 |
| 2,3,5-, 2,4,5-Trimethylphenols | 0.8 | 0.4 |
| 2,3,4-Trimethylphenol | — | 0.5 |
| Recovery of 2,3,6-Trimethylphenol | 48% | 74.5% |
| | Fraction B | Fraction B |
| Miscellaneous | 1.1 | 0.9 |
| 2,4-, 2,5-Xylenols | 6.8 | — |
| 2,3-, 3,5-Xylenols | 21.9 | — |
| 2,4,6-Trimethylphenol | 24.2 | 48.1 |
| 2,3,6-Trimethylphenol | 44.6 | 48.3 |
| 2,3,4-Trimethylphenol | 1.4 | 2.7 |
| Recovery of 2,3,6-Trimethylphenol | 46% | 23.1% |

Thus, in the above-described run, by the practice of the present invention, 74.5 percent of the 2,3,6-trimethylphenol in the feed to the caustic extraction zone was recovered in a purity of 95.4 percent, in contrast to the results of fractionation only of the feed, whereby only 48 percent of the 2,3,6-trimethylphenol in the feed was recovered in a purity of 95.3 percent, an improvement of over 50 percent in yield of the same purity.

According to the provisions of the patent statutes, we have explained the principle, preferred construction, and mode of operation of our invention and have illustrated and described what we now consider to represent its best embodiment. However, we desire to have it understood that, within the scope of the appended claims, the invention may be practiced otherwise than as specifically illustrated and described.

We claim:

1. In a process for distillatively recovering 2,3,6-trimethylphenol from a methylate product obtained by the methylation of phenol with methanol over activated alumina wherein the methylate product is subjected to a first fractionation to produce a first fraction containing at least 40 weight percent 2,3,6-trimethylphenol followed by subjecting said first fraction to a second fractionation to produce a high purity 2,3,6-trimethylphenol, the improvement therein of increasing the yield of the high purity 2,3,6-trimethylphenol by, prior to said second fractionation, subjecting said first fraction to sequential dissolution in a hydrocarbon solvent boiling in the range of 60° to 150° C and countercurrent extraction with an aqueous solution of an alkali metal hydroxide in an extraction zone, the concentration of alkali metal hydroxide in said aqueous solution as fed to the extraction zone being in the range of 2 and 10 weight percent and the ratio of moles of alkali metal hydroxide in said aqueous solution as fed to the extraction zone to moles of extractables being in the range of 0.9 to 2.0, said extraction being carried out under temperature conditions sufficient to assure retention of the 2,3,6-trimethylphenol in the solvent phase while in the extraction zone, and recovering the raffinate as the feed stream for said second fractionation.

2. The improvement of claim 1 wherein the first fraction comprises 2,3,6-trimethylphenol, 2,4,6-trimethylphenol and 2,3-xylenol as the major components.

3. The improvement of claim 1 wherein the hydrocarbon solvent is toluene and the alkali metal hydroxide is sodium hydroxide.

* * * * *